United States Patent
Sting et al.

(10) Patent No.: US 7,582,869 B2
(45) Date of Patent: Sep. 1, 2009

(54) SYSTEM AND METHOD FOR OPTICAL ANALYSIS

(75) Inventors: Donald W. Sting, New Canaan, CT (US); Jeffrey H. Saller, Milford, CT (US); Gregg Ressler, Shelton, CT (US)

(73) Assignee: SAS Photonics, LLC, Danbury, CT (US)

( * ) Notice: Subject to any disclaimer, the term of this patent is extended or adjusted under 35 U.S.C. 154(b) by 0 days.

(21) Appl. No.: 11/670,264

(22) Filed: Feb. 1, 2007

(65) Prior Publication Data

US 2008/0017799 A1  Jan. 24, 2008

Related U.S. Application Data

(63) Continuation of application No. 11/458,862, filed on Jul. 20, 2006, now abandoned.

(51) Int. Cl.
  *G01J 1/00* (2006.01)
(52) U.S. Cl. .................................. 250/336.1
(58) Field of Classification Search ............... 250/336.1
  See application file for complete search history.

(56) References Cited

U.S. PATENT DOCUMENTS

| | | | |
|---|---|---|---|
| 3,740,156 | A | 6/1973 | Heigl et al. |
| 3,999,867 | A | 12/1976 | Stabell |
| 4,415,809 | A | 11/1983 | Shields |
| 4,595,833 | A | 6/1986 | Sting |
| 4,717,827 | A | 1/1988 | Harvey |
| 5,552,604 | A | 9/1996 | Sting et al. |
| 5,703,366 | A | 12/1997 | Sting et al. |

(Continued)

FOREIGN PATENT DOCUMENTS

EP  1 102 057 A1  5/2001

(Continued)

OTHER PUBLICATIONS

Notification of Transmittal of the International Search Report and Written Opinion of the International Searching Authority for PCT Appl. No. PCT/US2007/073658, dated Mar. 10, 2008.

(Continued)

*Primary Examiner*—David P Porta
*Assistant Examiner*—Jessica L Eley
(74) *Attorney, Agent, or Firm*—Calfee, Halter & Griswold LLP

(57) ABSTRACT

An optical analysis system utilizing transmission spectroscopy for analyzing liquids and solids includes a source of optical energy, a sample, a movable optical energy transmission window, a fixed optical energy transmission window, and a detection system. The fixed transmission window remains fixed relative to the source of optical energy. The sample is selectively positioned between the movable and fixed optical energy transmission windows for analyzing the sample. The optical energy is transmitted through one of the windows, the sample, and the other window to obtain encoded optical energy as a result of transmitting the optical energy through the sample. A detection system receives the encoded optical energy for analysis. The movable optical energy transmission window is selectively movable relative to the fixed optical energy transmission window to repeatedly and precisely align and make readily accessible both windows and the sample.

30 Claims, 12 Drawing Sheets

U.S. PATENT DOCUMENTS

| | | | |
|---|---|---|---|
| 5,750,998 A | 5/1998 | Goldman | |
| 7,132,660 B2* | 11/2006 | Sjaunja | 250/343 |
| 2003/0050541 A1* | 3/2003 | Wuori | 600/316 |
| 2005/0192493 A1* | 9/2005 | Wuori | 600/322 |

FOREIGN PATENT DOCUMENTS

| | | |
|---|---|---|
| GB | 429242 A | 5/1935 |
| GB | 722967 A | 2/1955 |
| GB | 2 159 940 A | 12/1985 |
| WO | 9743619 | 11/1997 |
| WO | 2004034038 A1 | 4/2004 |
| WO | 2006058741 A1 | 6/2006 |

OTHER PUBLICATIONS

Written Opinion of the International Searching Authority for PCT Appl. No. PCT/US2007/073658, dated Mar. 10, 2008.

* cited by examiner

SYSTEM AND METHOD FOR OPTICAL ANALYSIS

This application is a continuation of pending U.S. patent application Ser. No. 11/458,862, filed Jul. 20, 2006, which is hereby incorporated by reference.

BACKGROUND

The present invention relates to infrared (IR) analysis of materials. It finds particular application in conjunction with transmission spectroscopy apparatus used during infrared analysis of liquid and solid phase materials by performing transmission spectroscopy analyses and will be described with particular reference thereto. It will be appreciated, however, that the invention is also amenable to other applications.

While performing an infrared analysis transmission spectroscopy experiment of liquid and solid phase materials, infrared energy is passed through a thickness of a material being analyzed. The thickness of the material is typically no more than 100 microns for mid-infrared analysis and no more than 2 centimeters for near-infrared analysis. For strongly absorbing liquids such as aqueous based solutions, the thickness for mid-infrared analysis is typically much smaller (e.g., typically between about 10 microns and about 20 microns). Other than the typical need to use longer path lengths, analytical procedures for near-infrared analyses of liquids are very similar to those used for mid-infrared analyses. An exception relates to the typical need of near-infrared analyses to analyze many more samples to develop a robust method.

Sealed transmission cells are typically used to analyze liquids via transmission spectroscopy in the mid-infrared region whereas cuvettes are typically used in the near-infrared region. Transmission cells are typically sealed with an amalgam, gaskets, or o-rings. Such cells are typically filled using syringes and Luer-lok fittings, whereby a syringe containing a sample is attached to the input side Luer-lok fitting, and an empty syringe is attached to the exit side Luer-lok fitting. The syringes are simultaneously manipulated with "push-pull" actions to completely fill the cell without air bubbles. Cleaning the cell is accomplished in a similar fashion, whereby a solvent, instead of the sample, is placed in one syringe, and the solvent is then push-pulled into the empty syringe. An additional step of passing dry air through the cell further removes trace amounts of sample and solvent. Alternatively, small diameter tubing is used, whereby a liquid is made to flow through the cell by means of a pump or piston device. Cleaning cells via this arrangement occurs by using a valve to route a cleaning solvent through the cell, or more tediously, by disassembling the cell, cleaning the components, and re-assembling.

The typical analytical procedure when using sealed cells is: (1) establishing an instrument reference; (2) performing an analysis of the material of interest; and (3) executing a "method" using the information obtained in steps (1) and (2) to determine specific characteristics of the material of interest.

The precision, accuracy, and reliability of analyses depend upon many factors. In that regard, any unintended or unaccounted for changes in the three steps described above likely result in erroneous results. For example, if the reference cell is not sufficiently clean, an erroneous reference is established. If any substantive portion of the optical path is subjected to typical atmospheric changes of water vapor, carbon dioxide, and trace environmental gases, significant analytical measurement errors may result. If there is any change in the optical path of the cell, quantitative spectroscopic results are compromised. Therefore, any substantive unaccounted for changes between the development of the method and the execution of the method, and/or between the establishment of a reference and analyzing the sample, produces compromised results.

Several infrared transmission spectroscopy cells have been developed to address specific issues. Mid-infrared analysis of strongly absorbing liquids (e.g., liquids requiring path lengths less than about 20 microns) has been more routinely performed by attenuated total reflection (ATR) infrared analysis, as opposed to infrared transmission analysis. ATR cells have become widely utilized because of their ease of use.

Although infrared ATR analysis overcomes the time and difficulty of inserting and completely removing a material for analysis, the ATR technique has two problems that are not easily overcome. First, when using the ATR technique, infrared energy only penetrates a few microns into the material being analyzed. Therefore, ATR cannot universally be used to analyze any material that separates, or is in any way different in the bulk of the material as opposed to the surface of the material. Second, while the ATR technique allows for the effective path length to be increased by increasing the number of internal reflections, other factors, such as the ATR material's absorption, or the amount or placement of the material being analyzed become dominating negative factors.

For these and other reasons, there remains a need for having an easy to use and clean transmission spectroscopy sampling apparatus for performing infrared transmission spectroscopy analyses. Prior art, by virtue of the time, care, and difficulties associated with inserting and completely removing materials in transmission cells, has significantly limited the commercialization of infrared transmission spectroscopy analyses. In general, it is time consuming and difficult to make precise, accurate, and reliable quantitative analyses of liquids, pastes, and mulls by infrared transmission spectroscopy. The primary purpose of this invention is to reduce the time and difficulty of performing infrared transmission spectroscopy analyses while maintaining, if not improving, precision, accuracy, and reliability.

The present invention provides a new and improved apparatus and procedure which addresses the above-referenced problems.

SUMMARY

An optical analysis system utilizing transmission spectroscopy for analyzing liquids and solids includes a source of optical energy, a sample, a movable optical energy transmission window, a fixed optical energy transmission window, and a detection system. The fixed transmission window remains fixed relative to the source of optical energy. The sample is selectively positioned between the movable and fixed optical energy transmission windows for analyzing the sample. The optical energy is transmitted through one of the windows, the sample, and the other window to obtain encoded optical energy as a result of transmitting the optical energy through the sample. A detection system receives the encoded optical energy for analysis. The movable optical energy transmission window is selectively movable relative to the fixed optical energy transmission window to repeatedly and precisely align and make readily accessible both windows and the sample.

BRIEF DESCRIPTION OF THE DRAWINGS

In the accompanying drawings which are incorporated in and constitute a part of the specification, embodiments of the invention are illustrated, which, together with a general description given above, and the detailed description given below, serve to exemplify the embodiments of this invention.

FIG. 7b illustrates the transmission sampling apparatus in a second cleaning and sample insertion/removal position in accordance with the second embodiment shown in FIG. 7a;

DETAILED DESCRIPTION OF ILLUSTRATED EMBODIMENT

Figure 1:
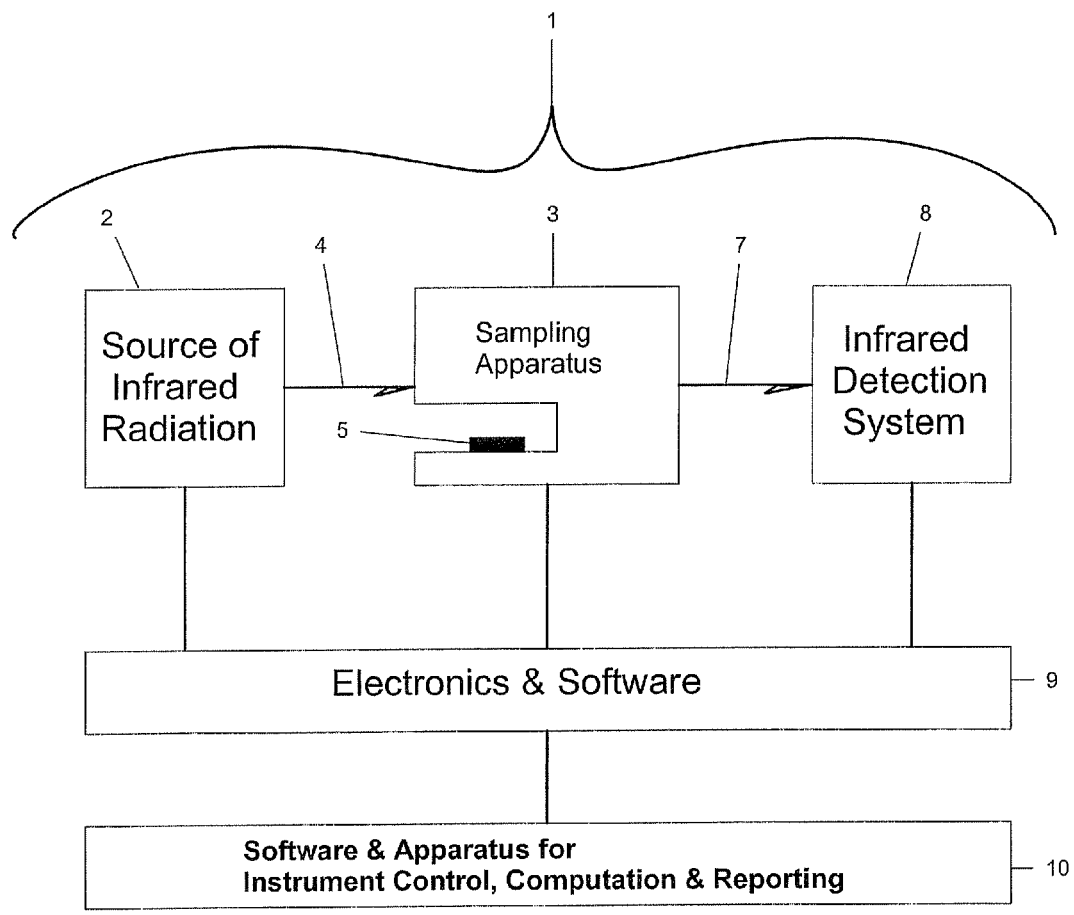
FIG. 1 illustrates a schematic representation of an infrared instrument system in accordance with one embodiment of the present invention.

With reference to FIG. 1, an infrared (IR) instrument system 1 utilizes transmission spectroscopy for performing optical analysis in one embodiment of the present invention. The system 1 includes a source of optical energy 2 (e.g., modulated infrared radiation from an FTIR) and a transmission spectroscopy sampling apparatus 3. A sample material/reference material 5 (e.g., a specimen) is positioned within the sampling apparatus 3. The sampling apparatus 3 directs infrared radiation 4 from the source 2 to the sample/reference material 5. In a transmission spectroscopy experiment, the infrared radiation passes through the transmission sampling apparatus 3 containing the sample/reference material 5 to create altered (encoded) infrared radiation 7. The sampling apparatus 3 directs the altered infrared radiation 7 to an infrared detection system 8. In the illustrated embodiment shown in FIG. 1, electronics and software 9 electrically communicates with the source of optical energy 2, the sampling apparatus 3, the detection system 8, and instrument control, computation, and reporting apparatus 10.

The source of infrared radiation 2, the detection system 8, the instrument electronics 9, and the instrument software and apparatus 10, including the functions of instrument control, computation, and reporting, have many variations that are well known in the art.

Figure 2:
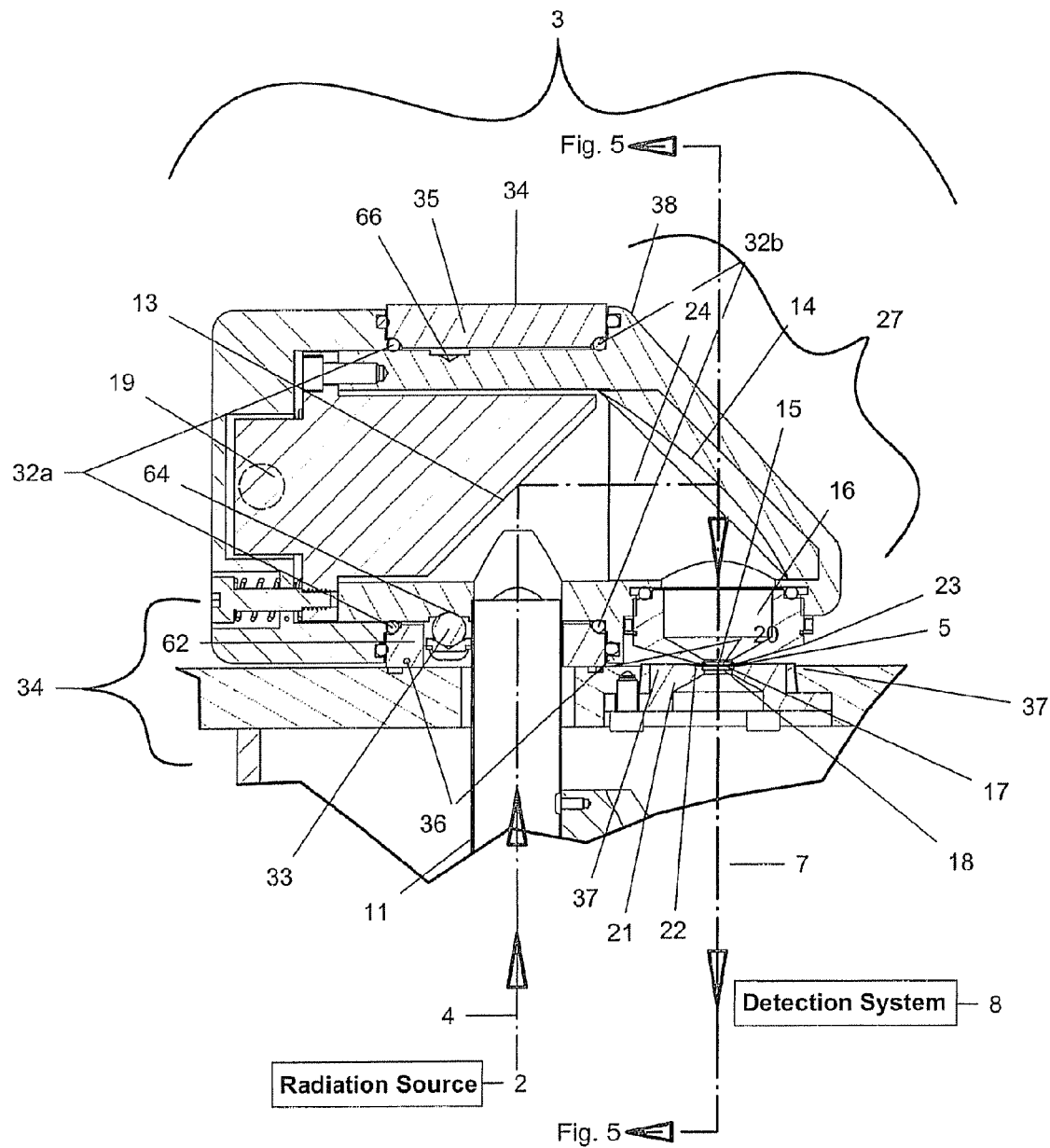
FIG. 2 illustrates a cross-sectional view in elevation of the transmission sampling apparatus in a first sampling position in accordance with one embodiment of an apparatus illustrating principles of the present invention.

FIG. 2 illustrates a cross-sectional elevation of one embodiment of the transmission sampling apparatus 3 in a first position, which is used for analysis. The infrared radiation path 4 is shown being received from the source of infrared radiation 2 through a light pipe 11 and into a chamber 12 in a movable apparatus or head 27. After exiting the light pipe 11, the infrared radiation 4 is redirected by a mirror 13 so as to be further redirected by a focusing mirror 14 to and through a movable optical energy (infrared) transmission window 15, fixedly mounted in the upper movable assembly 27, through the sample/reference material 5, to and through a fixed optical energy (infrared) transmission window 18, and to the detection system 8.

Figure 3A:
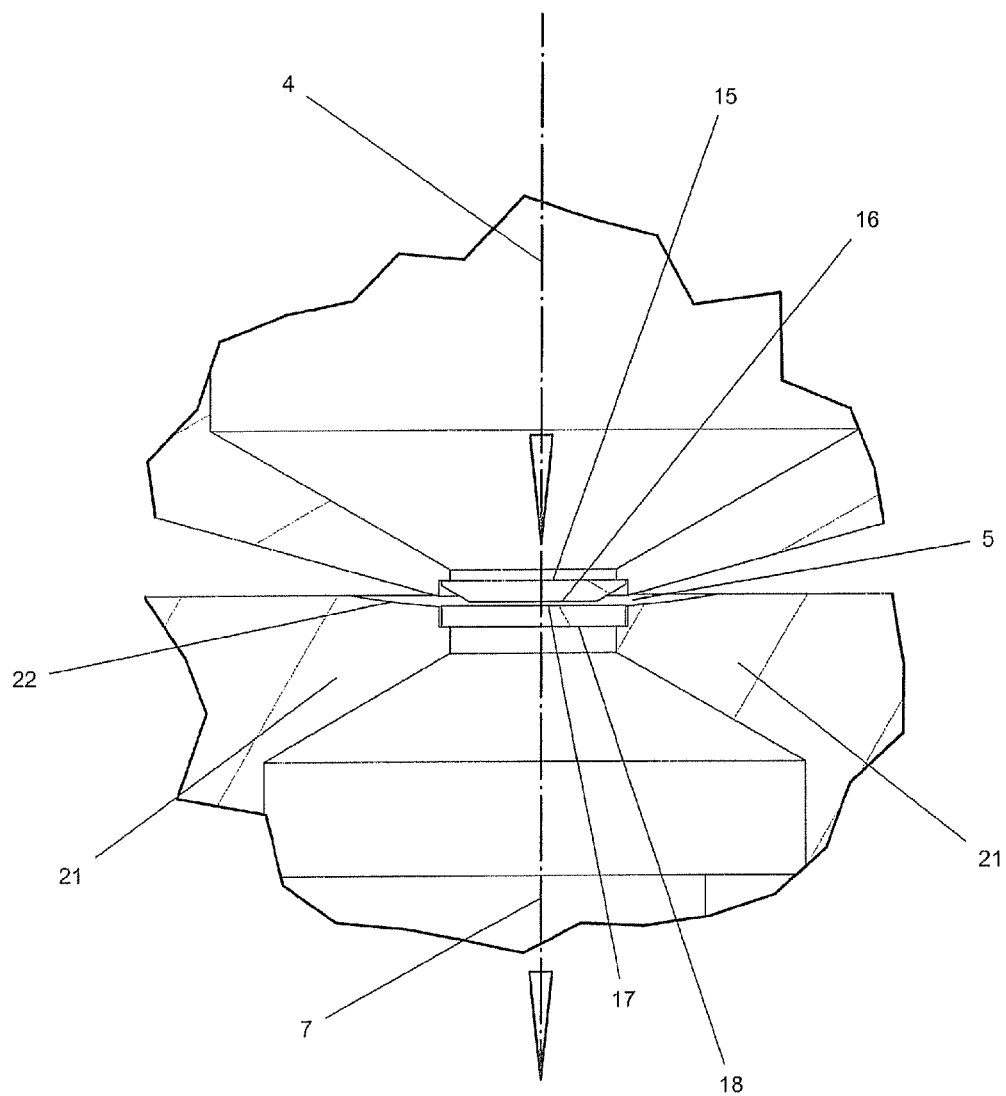
FIG. 3a illustrates an enlarged cross-sectional view of the sample positioned between the movable and fixed transmission windows in the sampling position, as shown in FIG. 2, in accordance with one embodiment of an apparatus illustrating principles of the present invention.
Figure 3B:
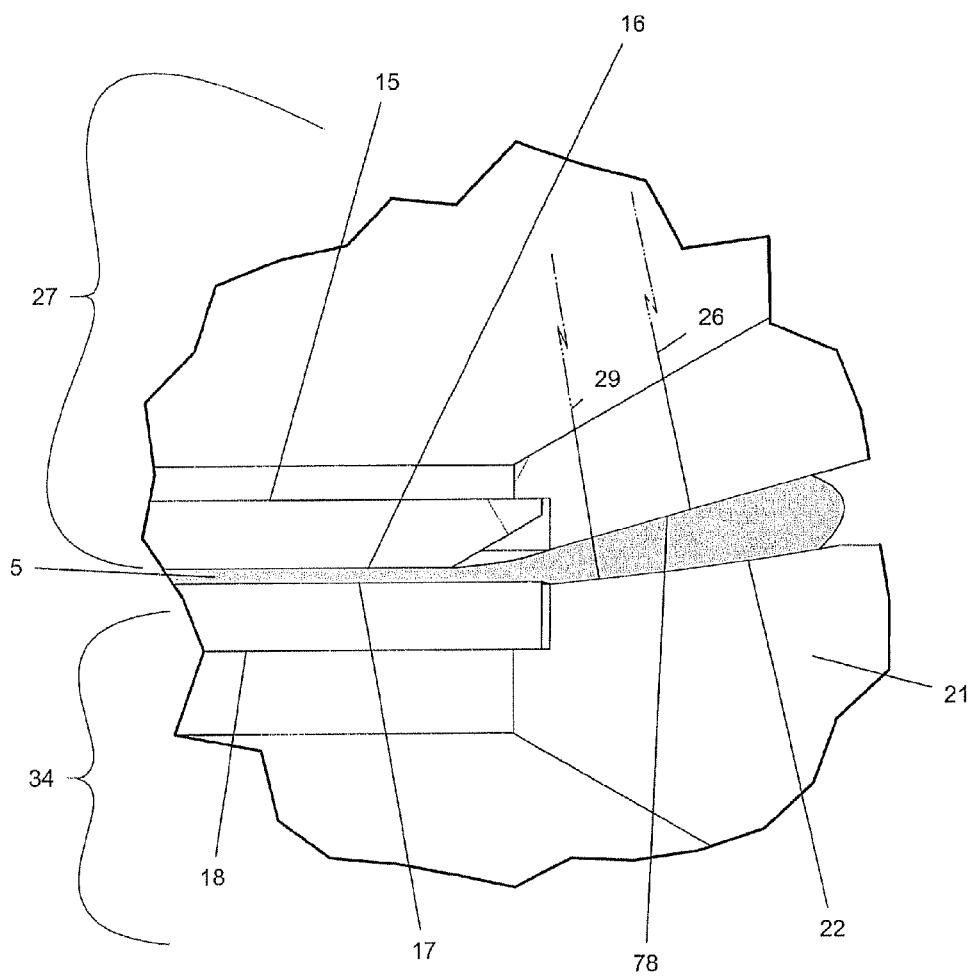
FIG. 3b illustrates a much further enlarged cross-sectional view of the sample positioned between the movable and fixed transmission windows in the sampling position, as shown in FIG. 2, in accordance with one embodiment of an apparatus illustrating principles of the present invention.

The movable infrared transmission window 15, which includes a sample contacting surface 16, is illustrated in FIGS. 2, 3a, and 3b in an analysis (sampling) position. In this position, the sample contacting surface 16 contacts the sample/reference material 5 (e.g., a liquid, mull, paste, melt, powder, and/or certain solid sample material, etc), which is sitting partially on an upwardly facing surface 17 of the fixed infrared transmission window 18 and partially on an adjoining generally spherical depression portion 22 formed in a retaining ring 21. The retaining ring 21 is received in and mounted to a top plate 20 of a fixed apparatus 34 of the sampling apparatus 3 (see FIG. 2). Therefore, it is evident that in the analysis (sampling) mode, the sample/reference material 5 is between the movable and fixed transmission windows 15, 18. In the illustrated embodiment, edges of the windows 15, 18 are not sealed to contain the sample 5 when in the sampling position. This embodiment is contemplated to be used with, for example, oil-based samples that are not highly volatile. However, other embodiments, in which a seal (e.g., an o-ring) is used around the upper edge of the depression 22 and further in contact with a nose piece assembly 23 to contain relatively volatile samples, are contemplated.

For better clarity, FIG. 3a shows a blown up section of the sampling area of the transmission spectroscopy sampling apparatus 3 shown in FIG. 2. FIG. 3b shows a further blown up section of the sampling area shown in FIG. 3a. With reference to FIGS. 2, 3a, and 3b, the downward facing sample contacting surface 16 of the movable transmission window 15 and the upwardly facing sample contacting surface 17 of the fixed transmission window 18 are shown in contact with the sample/reference material 5. Furthermore, the upward facing sample surface 17 is shown at the bottom of the shallow spherical depression portion 22 of the retaining ring 21. However, in other embodiments, the fixed, second window 18 is not in the bottom of depression 22, but is canted so as to allow gas bubbles to escape the sample/reference material 5 without affecting the infrared radiation 4. In such an embodiment, other changes would be required which would be well understood by those knowledgeable in the art.

Referring again to FIG. 2, the sampling apparatus 3 is broadly comprised of the movable apparatus 27 and the fixed apparatus 34. The movable apparatus 27 includes a rotatable housing 38, the mirrors 13, 14, the chamber 12, and the nose piece assembly 23, which further includes the movable infrared transmission window 15. In this manner, the transmission window 15 is fixedly secured to the movable apparatus 27, which rotates about an axis 24 by means of twisting lever 19. The fixed apparatus 34 includes a fixed housing 35, bearings/seals 32a, 32b, a spring loaded seated ball lock assembly 33, the instrument top plate 20, seals 36, 37, and the retaining ring 21. Retaining ring 21 includes the infrared transmission window 18 sealingly affixed thereto. In this manner, the transmission window 18 is fixedly secured to the fixed apparatus 34.

Figure 4:
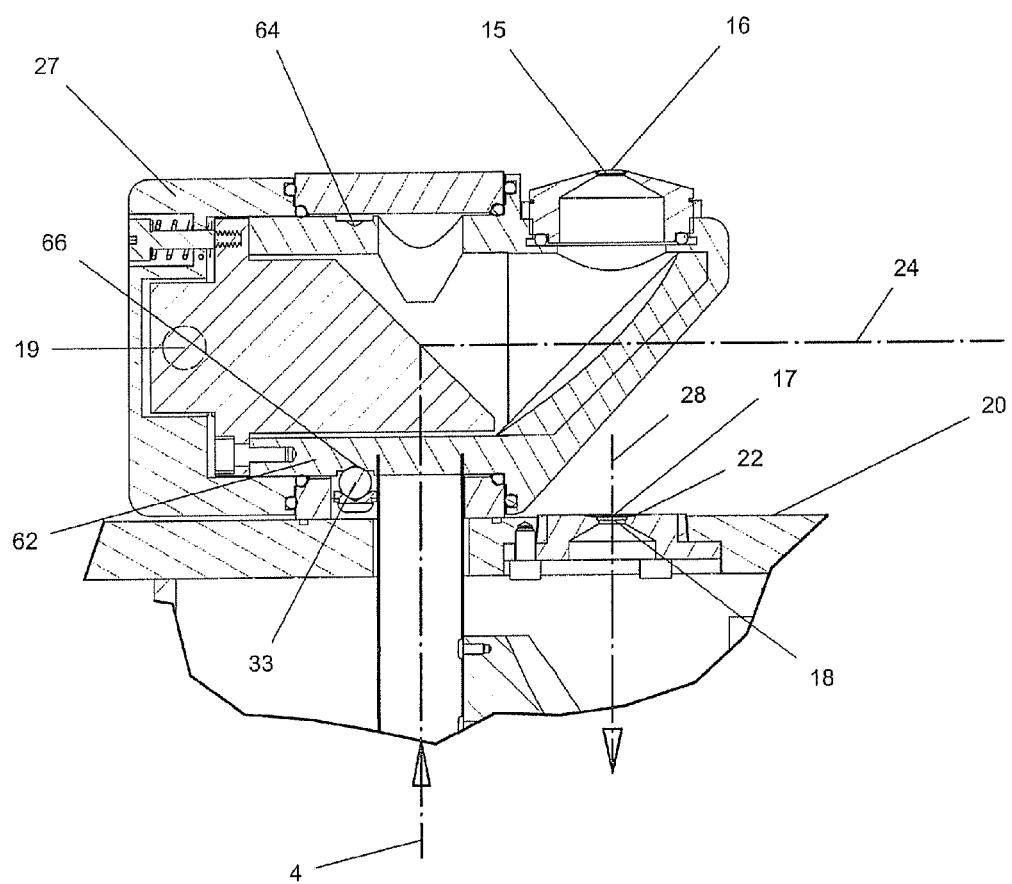
FIG. 4 illustrates a cross-sectional view of the transmission sampling apparatus in elevation similar to FIG. 2 but showing a second cleaning and sample insertion/removal position.

In the embodiment illustrated in FIGS. 2 and 4, portion 62 of the fixed apparatus 34 surrounds a portion of the movable apparatus 27 to movably couple the movable apparatus 27 and the fixed apparatus 34. As illustrated in FIGS. 2 and 4, the movable apparatus 27 selectively reliably rotates by means of turning the lever 19 relative to the fixed apparatus 34 on the bearings 32a, 32b about the axis 24 generally parallel to the top surface of the top plate 20 and the retaining ring 21. In the first, sampling position shown in FIG. 2, the movable transmission window 15 and fixed transmission window 18 are in optical alignment and have a separation which defines the optical path length of the sample/reference material 5 captured therebetween.

FIG. 4 illustrates a cross-sectional view of the sampling apparatus 3 in a second position used for inserting/removing the sample/reference material 5 and for cleaning the transmission windows 15, 18. The movable apparatus 27 is rotated 180° around the axis 24 from the first position shown in FIG. 2 using the lever 19. As shown in this orientation, the sample contacting surfaces 16, 17 of the movable and fixed infrared transmission windows 15, 18, respectively, are both upwardly facing and readily accessible for visible observation and cleaning with simple cleaning mechanisms such as clean cloths, Kim-wipes, or other such cleaning material. In one embodiment, the infrared transmission windows 15, 18 are made of diamond, silicon, cubic zirconium, sapphire, quartz and other hard surfaces and chemically resistant materials. However, all infrared transmission materials, as determined by the spectroscopic requirements for wavelength transmission, are also contemplated. When soft or easily damaged material such as NaCl, KBr, etc are used, extra care should be taken when cleaning to assure that damage does not occur to the transmission windows.

With reference to FIGS. 2 and 4, the movable apparatus 27 rotates relative to the fixed apparatus 34 on the interference fit bearings 32a, 32b to repeatedly and precisely move between the first position for sampling and the second position for inserting/removing the sample or reference material 5 and for cleaning the sample contacting surfaces 16 and 17 respectively of windows 15 and 18. An optical path, having a precisely repeatable path length, is created between the windows 15, 18 and captures the sample/reference material 5 whenever the movable apparatus 27 is in the first sampling position.

During use, a user causes the movable apparatus 27 to be rotated by the lever 19 to the sample insertion/removal position illustrated in FIG. 4 so that the spring loaded ball lock assembly 33 is secured in the detent 66. With the sampling apparatus 3 in this position, the movable and fixed transmission window surfaces 16, 17 are readily accessible to the user and may be cleaned, and a reference material 5 (e.g., air or any other suitable material) may be placed on the upwardly facing surface 17 of the fixed infrared transmission window 18. The user then causes the movable apparatus 27 to be rotated by lever 19 to the sampling position illustrated in FIG. 2 so that the ball lock assembly 33 is secured in the detent 64 circumferentially spaced from detent 66 by 180°. Infrared radiation 4 (see FIG. 1) is then passed through the light pipe 11 and is directed by the mirrors 13, 14 to pass through the reference material 5 along the optical path to create the encoded energy 7, which is detected by the detection system 8. The instrument electronics 9 (see FIG. 1) acquires, analyzes and stores characteristics of the encoded energy 7 from the known reference material 5 to calibrate the system.

The user then rotates the movable apparatus 27 by rotating the lever 19 back to the sample insertion/removal position illustrated in FIG. 4. At this point, the reference material 5 is removed, the window surfaces 16, 17 are cleaned, and a sample 5 is inserted on the fixed window surface 17 before the movable apparatus 27 is rotated again by the lever 19 to the sampling position illustrated in FIG. 2. As discussed above, the optical path length between the movable and fixed windows 15, 18 is maintained whenever the movable apparatus 27 is in the first sampling position. Once the sample 5 is positioned between the transmission windows 15,18, the infrared radiation 4 is passed through the sample 5 along the optical path to create the encoded energy 7, which is passed to the detection system 8. The encoded energy 7, which is encoded by the infrared absorption of the sample 5, is compared by the instrument electronics 9 to analyze and characterize the sample 5. The instrument software and apparatus 10 displays the results to a user. In one embodiment, the instrument electronics 9 includes software for predicting what material is included in the sample 5 as a function of the analysis. The prediction is then either reported to the user via the apparatus 10, or archived for future reference and/or reporting.

Because the optical path length is substantially the same whenever the movable apparatus 27 is in the sampling position illustrated in FIG. 2, calibration can be achieved by using the encoded energy, which is encoded by the known reference material, and various samples 5 may be analyzed by the calibrated instrument electronics 9 to identify various materials in different samples. Although the example discussed above is presented as utilizing the known reference material for calibration (e.g., analyzing the reference material) before analyzing the sample material, it is also contemplated to analyze the reference material for calibration at anytime including after analyzing the sample material or at periodic intervals. In addition, it is also contemplated to analyze a known reference material for calibration between analyzing two different samples.

Figure 5:
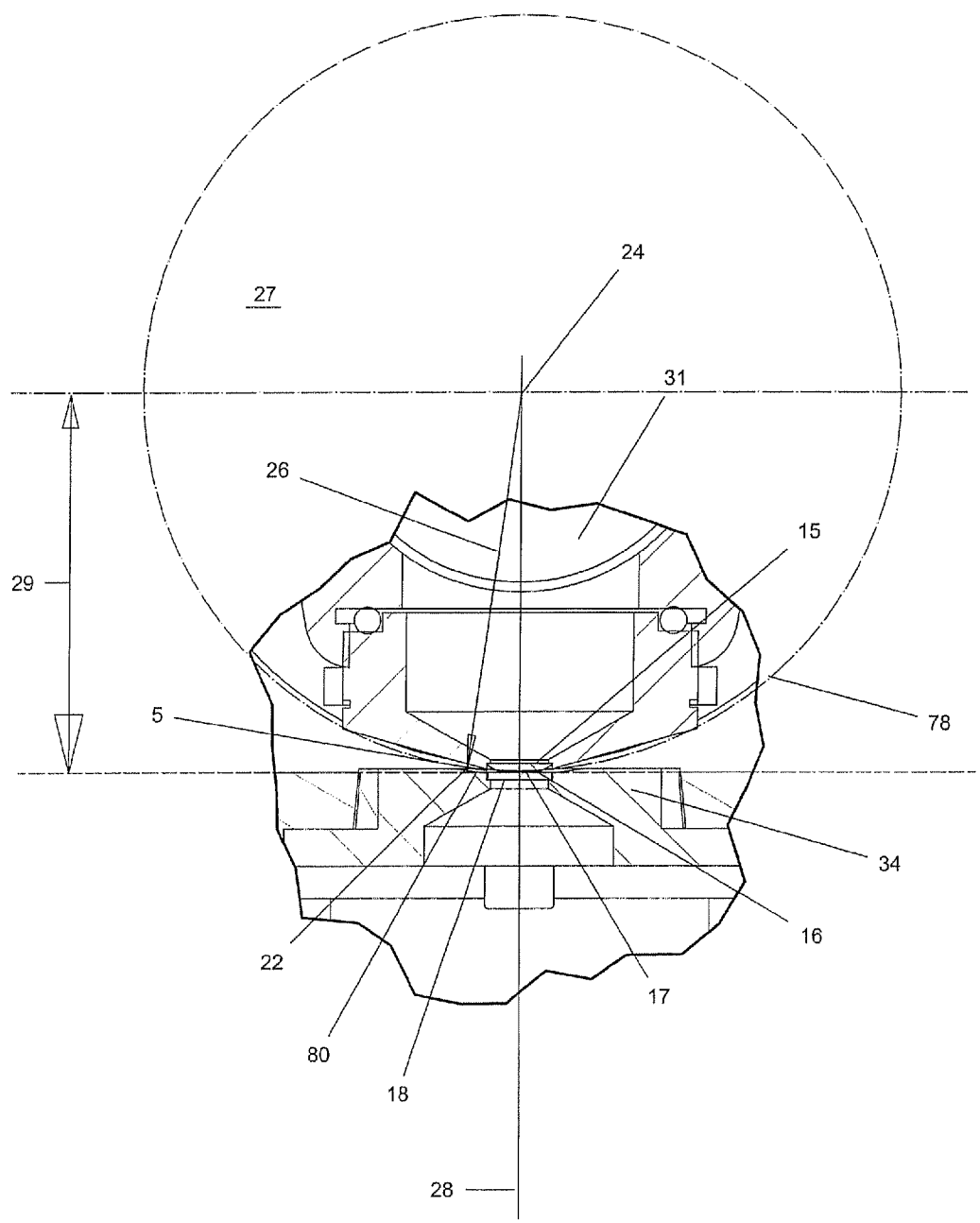
FIG. 5 illustrates an end cross-sectional view taken along the plane 5-5 in FIG. 2, showing the spherical depression portion in the fixed lower assembly.

FIG. 5 illustrates an end cross-sectional view of the spherical depression portion 22. The spherical depression portion 22 is centered on the infrared radiation optical centerline 28 with its center of curvature at the intersection of the optical centerline 28 and the axis of rotation 24. A radius 26 of the movable apparatus 27 from the axis 24 is less than the radius 29 of the spherical depression portion 22 from the axis 24 (also see FIG. 3b). This difference in radius magnitudes assures mechanical clearance between the movable apparatus 27 and the fixed apparatus 34. This clearance allows the movable apparatus 27 to be selectively rotated relative to the fixed apparatus 34 and to provide a sample containment space in the separation therebetween (see FIG. 3b). As illustrated in FIG. 5, the nose piece assembly 23 of the movable apparatus 27 includes a portion of a generally spherical surface portion 78 in which the movable transmission window 15 is mounted. The generally spherical surface portion 78 of the nose piece 23 is received in a second generally spherical surface portion 80 in the lower fixed apparatus 34 in which the fixed transmission window 18 is mounted. Sufficient clearance is provided between the spherical surface portions 78, 80 to form a separation which receives and contains the sample/reference material 5.

The movable apparatus 27 may be precisely repositioned for establishing an instrument calibration using a known reference or material or performing an experiment with the sample/reference material 5. In that regard, the embodiment illustrated in FIG. 2 includes the interference fit rotational bearing 32a, 32b and the spring loaded seated ball lock assembly 33. The movable apparatus 27 is rotated in a 180 degree rotational motion between the sampling position as shown in FIG. 2 and the sample insertion/removal and cleaning position as shown in FIG. 4 by rotating the lever 19. The spring loaded seated ball assembly 33 is housed in the fixed lower apparatus 34 and is spring biased upwardly into a spherical recess or detent 64 when in this sampling mode (see FIG. 2). The spring loaded ball assembly 33 is in a 180° circumferentially spaced second spherical recess or detent 66 when in the cleaning, sample replacement position (see FIG. 4). To selectively rotate the upper movable apparatus, the spring loaded seated ball assembly 33 is moved downwardly against the bias of the spring to remove the ball from the spherical recess or detent 64, 66 to allow rotation of the movable assembly. When the upper movable apparatus has been rotated 180°, the spring urges the spring loaded seated ball 33 into the detent 64, 66 aligned therewith to lock the upper movable apparatus in the selected position for precise and repeatable optical alignment in the first sampling position and for separation and exposure of the movable window surface 16 and fixed window surface 17 in the second position. While a detent assembly is illustrated in this embodiment, other embodiments are contemplated which use stops with magnets as an alternative method to achieve precise repositioning.

Figure 6A:
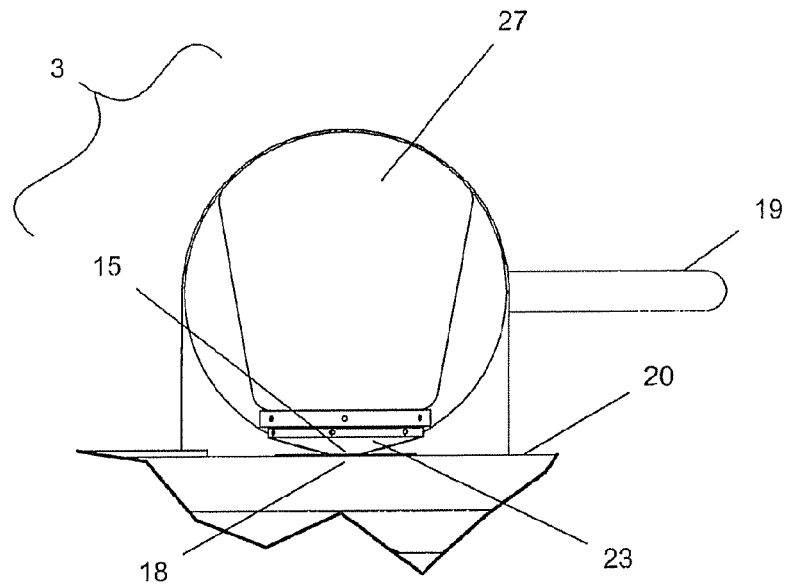
FIG. 6a illustrates a right end view of the transmission sampling apparatus in the first sampling position in accordance with FIG. 2

FIG. 6a shows a right end view of the apparatus 3 in the sampling position illustrated in FIG. 2. As shown, the nosepiece assembly 23 is pointing downward and faces the fixed transmission window 18 to perform infrared transmission analysis on a known reference material or sample contained between the two windows 15, 18.

Figure 6B:
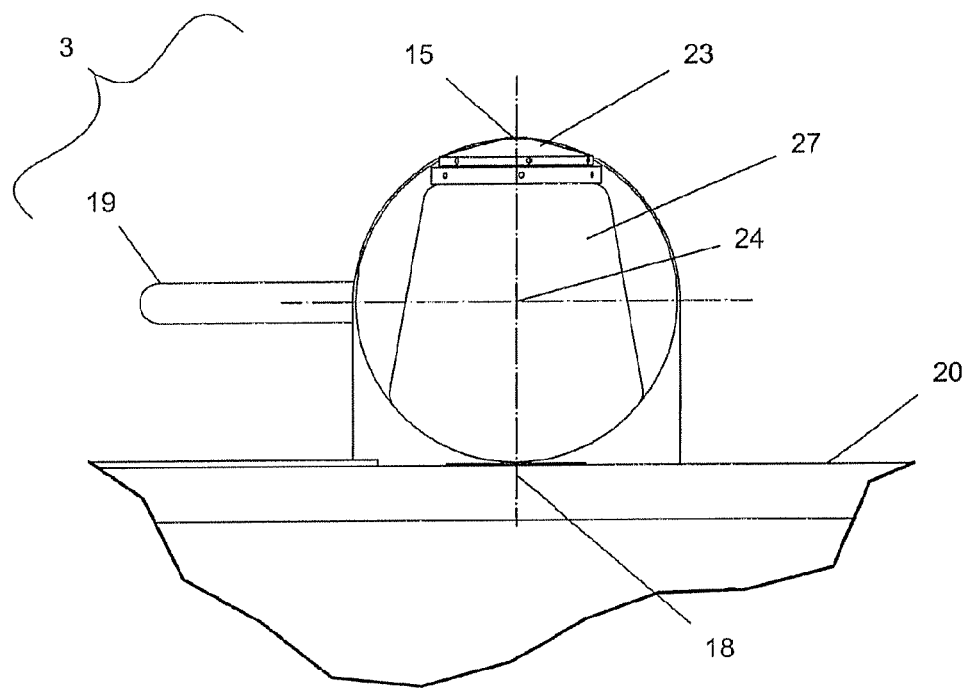
FIG. 6b illustrates a right end view of the transmission sampling apparatus in the second cleaning and sample removal/insertion position FIG. 4.

FIG., 6b shows a right end view of the apparatus in the position illustrated in FIG. 4. In this position, the nosepiece assembly 23 is facing upward or rotated 180 degrees from that shown in FIG. 6a. As discussed above, achieving the orientation in FIG. 6a is obtained by a single 180 degree rotation of the movable apparatus 27 by means of rotating lever 19. In such a position, both window surfaces 16, 17 are made readily accessible for cleaning and sample removal from or insertion on the lower fixed window 18. Moving from the orientation of FIG. 6b to FIG. 6a likewise requires only a 180 degree rotation of the movable apparatus 27, with no other movements or adjustments required. The spring loaded ball assembly 33 (see FIGS. 2 and 4) mounted in the fixed apparatus 34 (see FIGS. 2 and 4) cooperating with one or the other aligned detents 64, 66 (see FIGS. 2 and 4) in the movable apparatus 27 positively retains the movable apparatus 27 in the position selected.

Figure 7A:
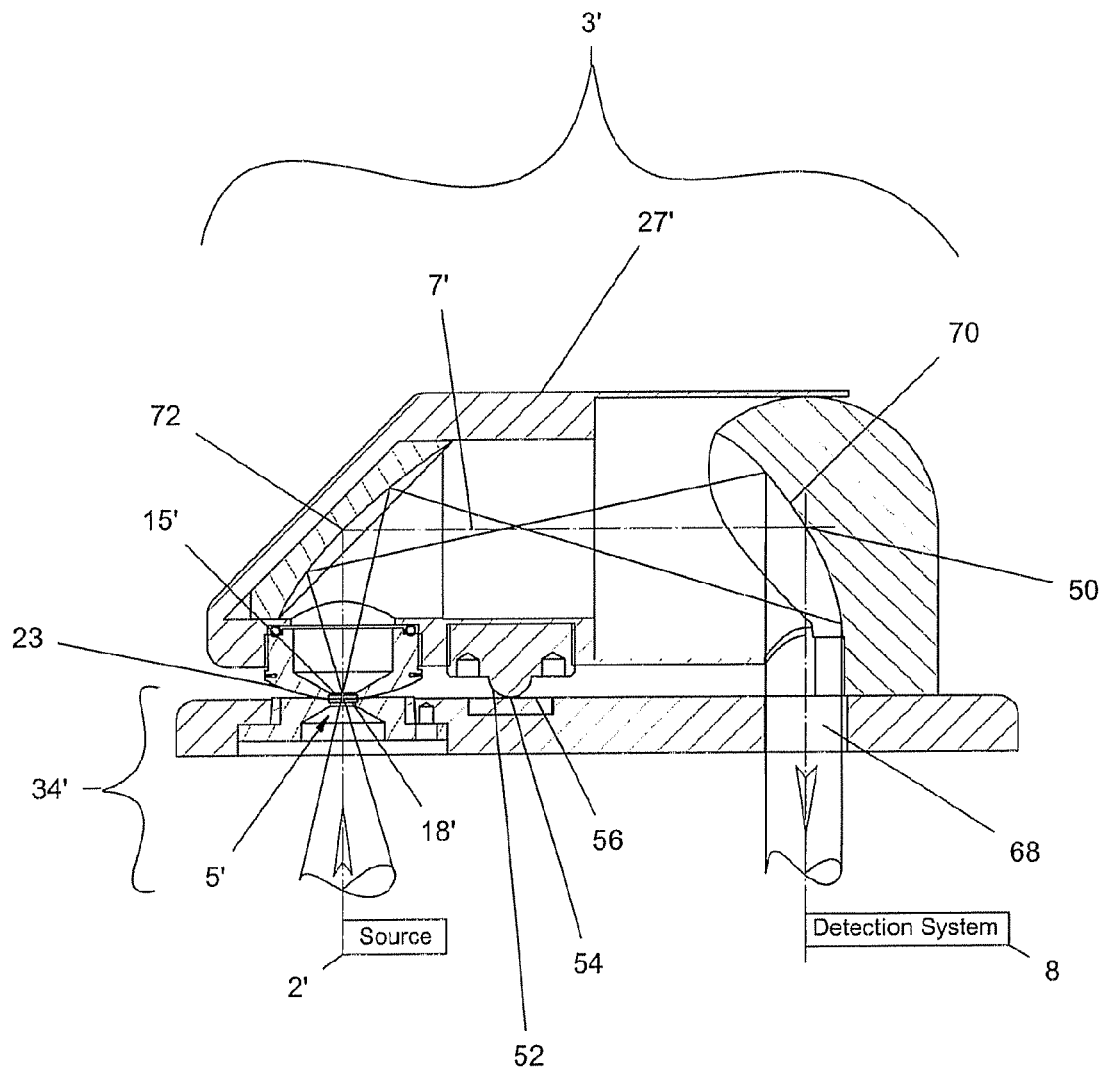
FIG. 7a illustrates a cross-sectional view in elevation of a transmission sampling apparatus in a first sampling position in accordance with a second embodiment of an apparatus illustrating principles of the present invention.
Figure 7B:
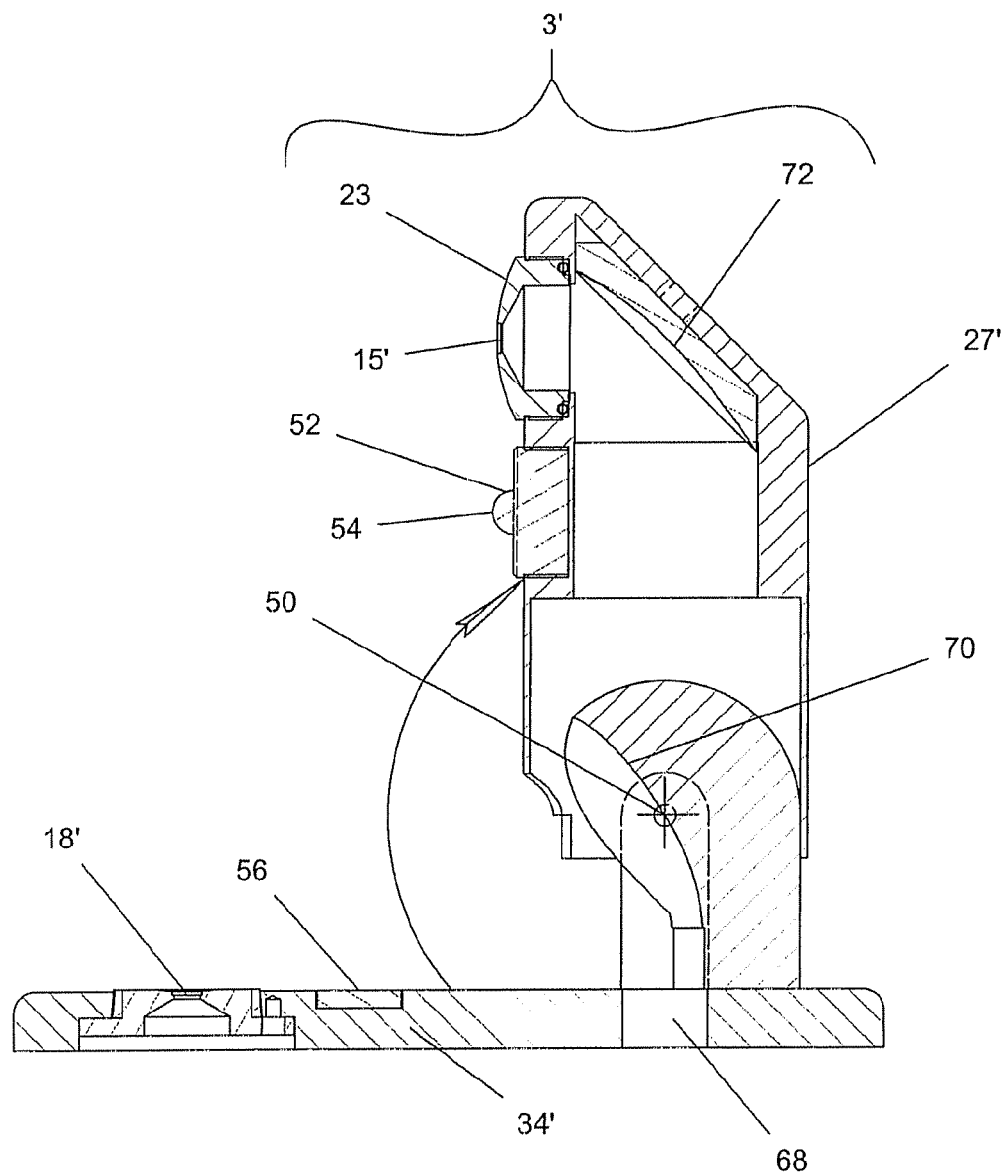

FIGS. 7a and 7b illustrate a second embodiment of the present invention. For ease of understanding this embodiment of the present invention, like components are designated by like numerals with a primed (') suffix and new components are designated by new numerals.

With reference to FIG. 7a, the transmission sampling apparatus 3' includes a hinge 50 connecting the upper movable apparatus 27' to the lower fixed apparatus 34'. In this embodiment, the movable apparatus 27' is an arm that pivots around the hinge 50. An adjustable setting device 52 (e.g., a set screw with a hardened ball projection) is positioned in the movable apparatus 27' for adjustably establishing a substantially repeatable path length of the transmission sampling apparatus 3' optical path, which may be adjusted as required for the specific material being analyzed. The adjustable setting device 52 includes a contact point 54 (e.g., a surface of a hardened ball) that, in the position illustrated in FIG. 7a, abuts against a surface 56 of the fixed apparatus 34'. In the illustrated embodiment, the surface 56 is a hardened magnetic insert in the fixed apparatus 34' that provides a positive reference, pulling the movable apparatus 27' into positive contact with the surface 56.

The contact point 54 is moved in or out of the moveable apparatus 27' to a desired position. For example, the user screws the adjustable setting device 52 in or out of the moveable apparatus 27' to the desired position. The adjustable setting device 52 remains at the desired position until the user screws the adjustable setting device 52 in or out of the moveable assembly 27' to a new desired position. When the movable apparatus 27' is positioned as illustrated in FIG. 7a, the contact point 52 abuts against the surface 56 and is positioned for establishing a reference and performing an analysis. Once the contact point 52 is set in the movable apparatus 27', the transmission assembly optical path remains substantially the same even after the moveable apparatus 27' is repeatedly pivoted around the hinge 50 and returned to the position illustrated in FIG. 7a.

With respect to the optical path in FIG. 7a, focused optical energy from the source 2' passes through the fixed window 18', the sample 5', the movable window 15' continuing on to mirror 72 which redirects the encoded optical energy 7' to mirror 70, through aperture 68 in the fixed assembly 34' and to the detection system 8'.

FIG. 7b illustrates the movable apparatus pivoted approximately 90° about hinge point 50 to a second position substantially perpendicular to the fixed lower apparatus 34'. In this second position, the movable and fixed windows 15', 18', respectively, are exposed to the user. As such, the apparatus 3' is in the position for insertion/removal of the sample/reference material 5' (see FIG. 7a) and for cleaning the infrared transmission windows 15', 18' and other sample contacted areas.

Other embodiments for easily changing the separation between the two infrared transmitting windows (and the path length) are also contemplated. For example, an apparatus similar to that used on microscope objectives, which correct for slide thickness, is contemplated for changing the path length. Many such options exist to change the path by microns (as is the case of mid-infrared analysis) or more than a couple of centimeters (as in the case of near-infrared analysis).

Figure 8A:
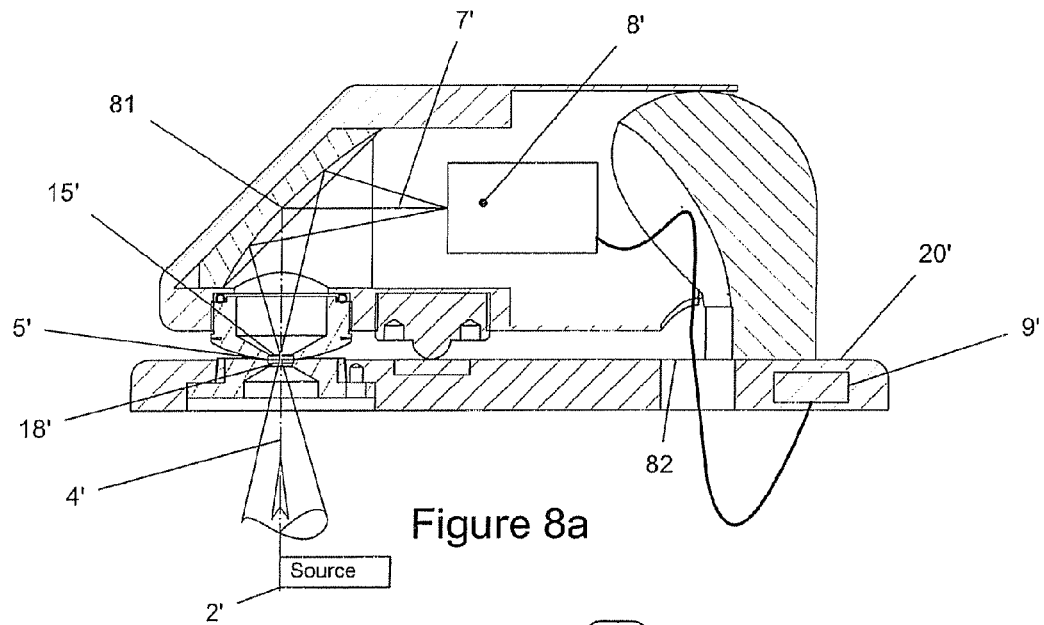
FIGS. 8a and 8b illustrate a transmission sampling apparatus in accordance with a fourth embodiment of an apparatus illustrating principles of the present invention with the sample analysis position shown in FIG. 8a and the cleaning and sample insertion removal position shown in FIG. 8b.
Figure 8B:
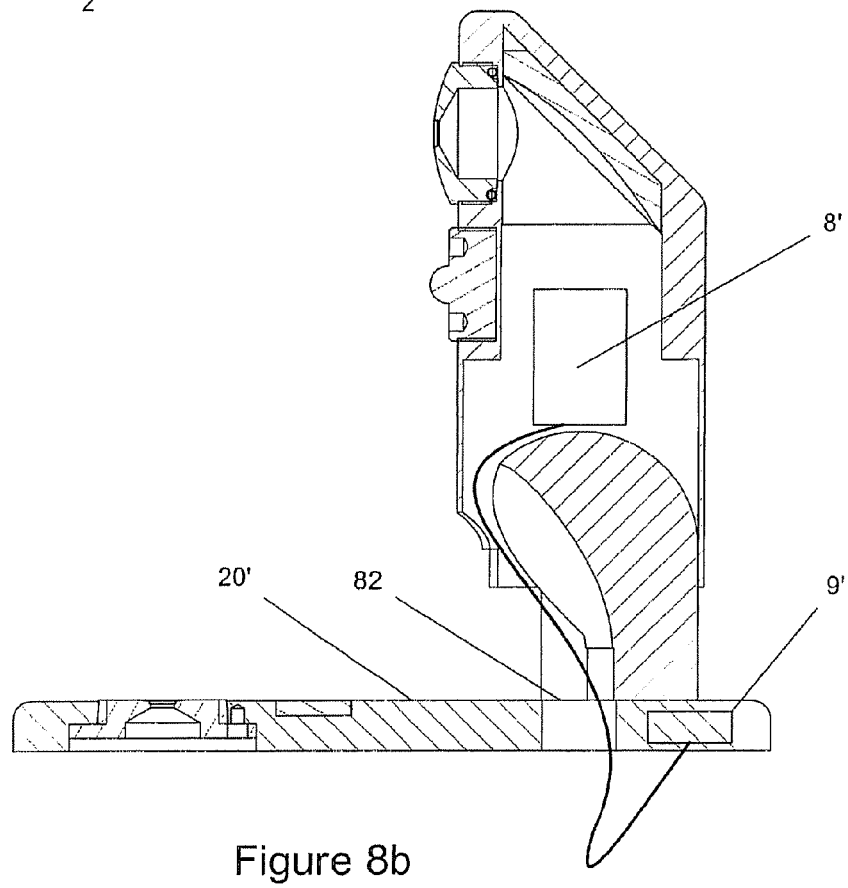

FIGS. 8a and 8b illustrate the transmission sampling apparatus 3' shown in FIGS. 7a and 7b in which the detection system 8 is incorporated into the movable apparatus 27'. With reference to FIGS. 8a and 8b, electrical and electronic signals are communicated between the detection system 8', which is embedded in the movable apparatus 27', and the electronics and software 9', which is housed in the fixed apparatus 34'. The electrical cables are fed through a sealed hole 82 in the top plate 20' of the transmission sampling apparatus 3'. Focused optical energy 4' from the source 2' passes through the fixed window 18', the sample/reference material 5', the movable window 15' continuing on to mirror 81, which redirects the encoded optical energy 7' to the detection system 8'. FIG. 8b illustrates the movable apparatus 27' in the position for cleaning the window surfaces 16', 17' and inserting a new sample/reference material 5'. Although only the embodiment illustrated in FIGS. 8a and 8b illustrate the detection apparatus 8' incorporated into the movable apparatus 27', it is to be understood that any of the other contemplated embodiments may include a detection system housed in the moveable apparatus and/or the electronics and software housed in the fixed apparatus.

Figure 9A:
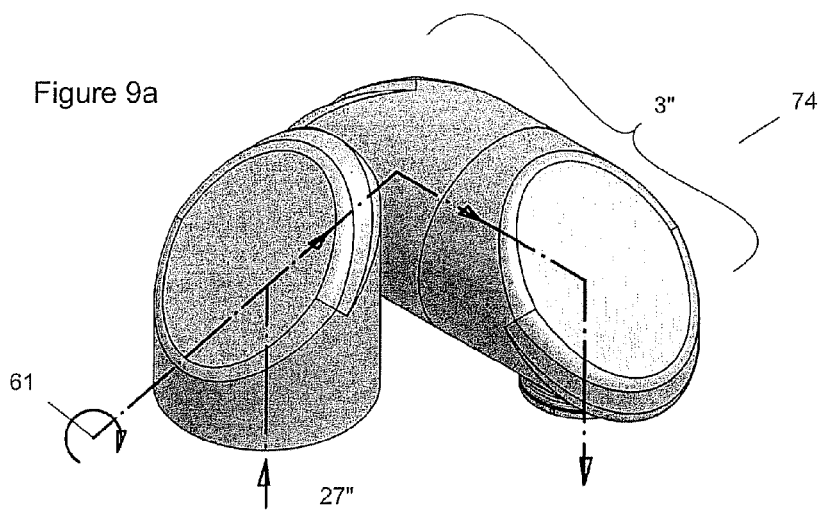
FIGS. 9a, 9b, and 9c illustrate a transmission sampling apparatus in accordance with a third embodiment of an apparatus illustrating principles of the present invention with the sample analysis position shown in FIGS. 9a and 9b and the cleaning and sample insertion removal position shown in FIG. 9c.
Figure 9B:
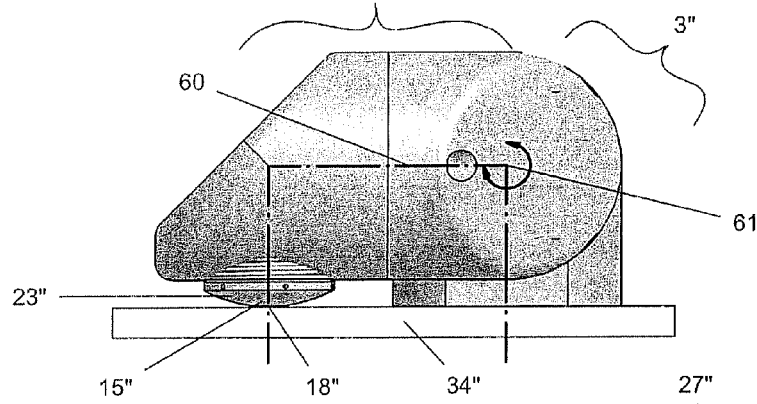
Figure 9C:
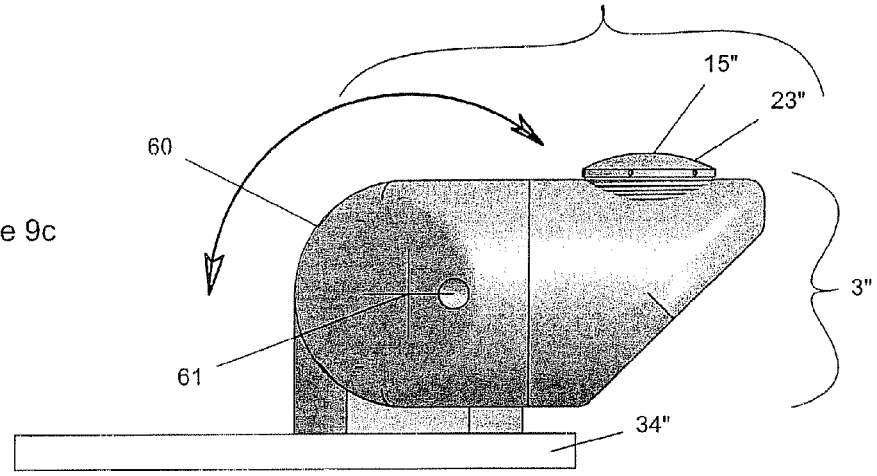

FIGS. 9a, 9b, and 9c illustrate a third embodiment of the present invention. For ease of understanding this embodiment of the present invention, like components are designated by like numerals with a double-primed (") suffix and new components are designated by new numerals.

FIG. 9a shows an isometric view of the apparatus 3". FIG. 9b shows a side view looking in the direction of arrow 74 in FIG. 9a, with the apparatus 3" in the position for aligning the movable transmission window 15" in the nose piece assembly 23" with the fixed transmission window 18" in the fixed apparatus 34" for instrument calibration and performing a sample analysis. FIG. 9c shows a side view with the apparatus 3" in the sample insertion/extraction and cleaning position. Like the embodiment discussed above in FIGS. 7a and 7b, the embodiment illustrated in FIGS. 9a, 9b, and 9c uses a circumferential rotational bearing 60 that rotates about the centerline 61. However, the embodiment illustrated in FIGS. 9a, 9b, and 9c differs from the first embodiment mainly in the way the movable infrared transmission window 15" is brought into contact with the sample/reference material 5". More specifically, the motion of the moveable apparatus 27" around the centerline 61 causes the transmission window 15" to be positioned over the sample/reference material 5" before coming into contact with the sample/reference material 5". Therefore, the motion of the moveable apparatus 27" is somewhat similar to the motion of the moveable apparatus 27' (see FIGS. 7a and 7b). On the other hand, the motion of the moveable apparatus 27" is substantially different than the motion of the moveable apparatus 27 (see FIGS. 2 and 4) of the first embodiment, which exhibits a sliding or shearing motion relative to the sample/reference material 5 (see FIGS. 2 and 4). The choice of the specific embodiment depends upon tradeoffs between simplicity, total optical path, costs, as well as the relationship between other aspects of the instrument design, and in certain cases the properties of the sample. The differences exhibited in the embodiment illustrated in FIGS. 9a, 9b, and 9c do not detract from the spirit of the invention.

Figure 10:
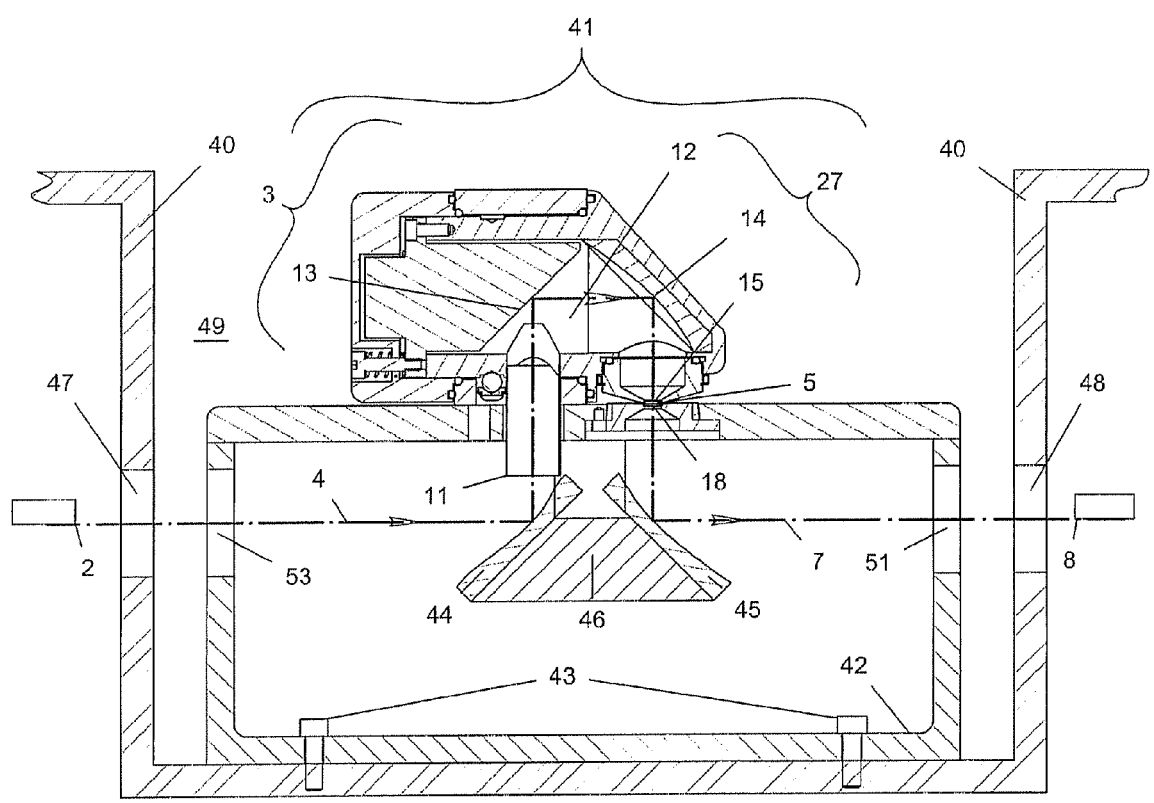
FIG. 10 illustrates a side cross-sectional view of the transmission sampling apparatus of FIGS. 1-4 used as an accessory to a general purpose Fourier Transform Infrared (FTIR) instrument.

FIG. 10 illustrates a side cross-sectional view of the sampling apparatus 3, which is illustrated in FIGS. 2 and 4, used as an accessory to a general purpose Fourier Transform Infrared (FTIR) instrument 41. With reference to FIG. 10, the infrared radiation 4 is produced by the source 2. The radiation 4 passes through an orifice 47 in a cover 40 and enters into a sample compartment 49. The entering radiation 4 further passes through an orifice 53 in an accessory frame 42 and is redirected by a focusing mirror 44 through the light pipe 11 and into the chamber 12. Once in the chamber 12, the infrared radiation 4 is redirected by the mirror 13 to the concave focusing mirror 14. The focusing mirror 14 further redirects the infrared radiation 4 to and through the movable infrared transmission window 15, through the sample/reference material 5, and through the fixed transmission window 18. The infrared radiation is focused in the sample/reference material 5. Infrared radiation 7 is encoded as a result of passing infrared radiation 4 through the sample/reference material 5 to obtain encoded optical characteristics of the sample based upon the infrared energy absorbed by the sample/reference material 5. Alternatively, the system may be calibrated by passing infrared energy through a known reference material between the transmission windows to compare the obtained spectrum at the detector to the known spectrum for the reference material. The encoded infrared energy exits the transmission window 18. The encoded infrared radiation 7 is reflected off a detector matching mirror 45, which refocuses and redirects the encoded infrared radiation 7 through orifices 51, 48, respectively, and on to the infrared detection system 8 (see FIGS. 1 and 2). A mirror mount 46 in conjunction with mounting fasteners 43 provide further adjustment to align the accessory (apparatus) 3 to the instrument 41. Once the accessory is aligned to the instrument 41 and its source 2 and detector 8, the accessory 3 remains fixed except for the movable apparatus 27. The instrument 41, along with the accessory (transmission sampling apparatus) 3 can then be used in the fashion previously described.

There are many general purpose instruments in commercial use, and likewise many different optical configurations utilized. One skilled in the art understands the requirements and trade-offs required to match an accessory to a specific instrument. The specific set of interface mirrors 44, 45 are not intended to be used universally for all such instrument/accessory interfaces. For this reason, it is to be understood that the lack of disclosure of any specific interface mirrors 44, 45 is not intended to detract from the universal nature of the benefits derived from this invention.

It is contemplated that the FTIR functions in both the near-infrared and mid-infrared regions. However other embodiments of the present invention are also contemplated for use with all near-infrared and/or mid-infrared spectroscopic systems and is in no way limited to FTIR systems.

While the present invention has been illustrated by the description of embodiments thereof, and while the embodiments have been described in considerable detail, it is not the intention of the applicants to restrict or in any way limit the scope of the appended claims to such detail. As one example, for those skilled in the art, it is well known that sources of optical energy can be exchanged with detection systems without detriment to optical functionality. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. An optical analysis system utilizing transmission spectroscopy for analyzing specimens of at least one of liquids and solids, comprising:
   a source of optical energy;
   a specimen;
   a movable optical energy transmission window;
   a fixed optical energy transmission window, whereby the fixed transmission window remains fixed relative to the source of optical energy, the specimen selectively being positioned between the movable and fixed optical energy transmission windows and directly contacting both the movable and fixed optical energy transmission windows for analyzing the specimen, the optical energy being transmitted through one of the windows, the specimen, and the other window to obtain encoded optical energy as a result of transmitting the optical energy through the specimen; and
   a detection system for receiving the encoded optical energy for analysis, the movable optical energy transmission window being selectively movable relative to the fixed optical energy transmission window to repeatedly and precisely produce an optical path length between the movable and fixed windows and to repeatedly and precisely align and make readily accessible both windows and the specimen.

2. The optical analysis system of claim 1 wherein the source of optical energy provides infrared optical energy.

3. The optical analysis system of claim 2, wherein the infrared optical energy is in the mid-infrared range.

4. The optical analysis system of claim 1, further including:
a movable apparatus, the movable transmission window being fixedly secured to the movable apparatus; and
a fixed apparatus, the fixed transmission window being fixedly secured to the fixed apparatus, the movable apparatus being movably coupled to the fixed apparatus, movement of the movable assembly to a first position repeatedly and precisely aligning the movable transmission window relative to the fixed transmission window for passing the optical energy through one of the windows, the specimen, and the other window during a transmission specimen analysis, and movement of the movable apparatus to a second position making readily accessible both windows and the specimen.

5. The optical analysis system of claim 4, further including:
an inlet in the movable apparatus to pass the optical energy therethrough into a chamber in the movable apparatus; and
a mirror mounted in the chamber to direct the incoming optical energy from the inlet to the movable transmission window.

6. The optical analysis system of claim 5, further including:
an outlet in the movable apparatus to pass the optical energy therethrough out of the chamber in the movable apparatus, at least one mirror mounted in the chamber to direct the optical energy from the movable transmission window to the outlet.

7. The optical analysis system of claim 1 including:
a moveable apparatus including the moveable transmission window;
a fixed apparatus including the fixed transmission window; and
a bearing assembly secured between the moveable apparatus and the fixed apparatus, the moveable apparatus rotating within a portion of the fixed apparatus.

8. The optical analysis system of claim 7, wherein the movable window slides into and out of the specimen.

9. The optical analysis system of claim 8, wherein the movable apparatus includes:
a projecting nose piece assembly with a substantially convex spherical surface portion in which the movable transmission window is mounted, the substantially convex spherical surface portion being received in a substantially concave spherical surface portion in the fixed apparatus in which the fixed transmission window is mounted, sufficient clearance being provided between the two spherical surface portions to provide a space for receiving and containing the specimen while the path length between the fixed window and the movable window.

10. The optical analysis system of claim 1, including:
a moveable apparatus including the moveable transmission window;
a fixed apparatus including the fixed transmission window; and
a hinge pivotally securing the moveable apparatus to the fixed apparatus, the moveable apparatus pivoting around the hinge when moving relative to the fixed apparatus to position the movable apparatus in optical alignment with the fixed transmission window.

11. The optical analysis system of claim 10 wherein the detection system is affixed to the movable apparatus.

12. The optical analysis system of claim 10, wherein the movable transmission window is positioned over the specimen before contacting the specimen.

13. A sampling apparatus for infrared transmission analysis of a specimen of at least one of a liquid and a solid, comprising:
a movable infrared transmission window;
a fixed infrared transmission window;
wherein the movable infrared transmission window has a first position repeatedly and precisely located relative to and spaced from the fixed infrared transmission window, a specimen contained in the space between, and directly contacting, the movable and fixed windows in said first position, infrared energy in the mid-infrared range transmitted through one of the windows, the specimen, and the other window resulting in infrared energy that is encoded with infrared characteristics of the specimen; and
wherein the movable infrared transmission window has at least a second position relative to the fixed window for exposing both the windows to permit removal of the specimen from the fixed window, cleaning of both windows, and placement of a new specimen on the fixed transmission window.

14. The sampling apparatus for infrared transmission analysis as set forth in claim 13, further including:
a movable apparatus, the movable window being fixedly secured to the movable apparatus;
a fixed apparatus, the fixed window being fixedly secured to the fixed apparatus; and
a portion of the fixed apparatus selectively extending into a first detent in the movable apparatus to secure the movable apparatus to the fixed apparatus in the first position and selectively extending into a second circumferentially spaced detent in the movable assembly when the first movable transmission window is in its second position.

15. The sampling apparatus for infrared transmission analysis as set forth in claim 14 further including:
a detection system affixed to and part of the movable apparatus.

16. The sampling apparatus for infrared transmission analysis as set forth in claim 14, wherein the movable apparatus is rotationally mounted to the fixed apparatus to permit the movable apparatus selectively to rotate about an axis that is substantially parallel to the fixed apparatus between the first and second positions of the first movable transmission window.

17. The sampling apparatus for infrared transmission analysis as set forth in claim 16, wherein the movable window shears the specimen as the movable window is moved into the first position.

18. The sampling apparatus for infrared transmission analysis as set forth in claim 14, further including:
an adjustable setting device for adjustably establishing the first position of the movable transmission window relative to the fixed transmission window.

19. The sampling apparatus for infrared transmission analysis as set forth in claim 13, further including:
a movable apparatus, the movable window being fixedly secured to the movable apparatus;
a fixed apparatus, the fixed window being fixedly secured to the fixed apparatus; and
a hinge pivotally securing the movable apparatus to the fixed apparatus, the movable apparatus pivoting around the hinge when the movable window is moved between the first and second positions.

20. The sampling apparatus for infrared transmission analysis as set forth in claim 19, wherein the movable apparatus includes at least one mirror operative to deliver the infrared energy from an optical inlet in the movable apparatus to the movable transmission window in its first position, the specimen, and the second fixed transmission window.

21. A method for performing an infrared transmission analysis of a specimen of at least one of a liquid and a solid, the method comprising:
  defining an optical path, including a repeatable path length, between a source of optical energy and a detection system through a transmission sampling apparatus including a movable transmission window, a specimen, and a fixed optical transmission window, the specimen directly contacting both the movable and fixed windows;
  passing optical energy along the optical path through the transmission sampling apparatus to obtain optical energy encoded with characteristics of the specimen;
  analyzing the encoded optical energy in a detection system to analyze the specimen; and
  selectively exposing the first and second windows for specimen extraction/insertion and maintaining the windows.

22. The method for performing an infrared transmission analysis of a specimen as set forth in claim 21, wherein the defining step includes:
  setting the movable optical transmission window to a first position relative to the fixed transmission window, the specimen being between the movable and fixed windows when the movable window is in the first position.

23. The method for performing an infrared transmission analysis of a specimen as set forth in claim 22, wherein the exposing step includes:
  setting the movable optical transmission window to a second position relative to the fixed transmission window, the windows being separated from one another and exposed to the user when the movable window is in the second position.

24. The method for performing an infrared transmission analysis of a specimen as set forth in claim 23, wherein setting the movable window to the first position and setting the movable window to the second position include:
  moving the movable window relative to the fixed window.

25. The method for performing an infrared transmission analysis of a specimen as set forth in claim 21, wherein defining the optical path includes:
  positioning the movable window in optical alignment with the specimen.

26. The method for performing an infrared transmission analysis of a specimen as set forth in claim 21, further including:
  adjusting the repeatable path length between the movable and fixed windows.

27. The method for performing an infrared transmission analysis of a specimen as set forth in claim 21, further including:
  mounting the movable window in a movable apparatus and the fixed window in a fixed apparatus.

28. The method for performing an infrared transmission analysis of a specimen as set forth in claim 27, further including:
  rotating the movable apparatus relative to the fixed apparatus.

29. The method for performing an infrared transmission analysis of a specimen as set forth in claim 28, further including:
  selectively retaining the movable assembly in a first position in which the movable window is in optical alignment with and closely spaced to the fixed window and in a second position in which the movable window is separated from the fixed window to permit window maintenance and specimen insertion and removal.

30. The method for performing an infrared transmission analysis of a specimen as set forth in claim 27, further including:
  pivoting the movable apparatus relative to the fixed apparatus.

* * * * *